United States Patent [19]

Maurer et al.

[11] 4,118,486
[45] Oct. 3, 1978

[54] COMBATING ARTHROPODS WITH O-METHYL-O-N-PROPYL-O-(2-CARBALKOXY-2-ALKOXY-VINYL)-THIONOPHOSPHORIC ACID ESTERS

[75] Inventors: Fritz Maurer; Hans-Jochem Riebel, both of Wuppertal; Wolfgang Behrenz, Untergruendemich; Ingeborg Hammann, Cologne, all of Germany

[73] Assignee: Bayer Aktiengesellschaft, Leverkusen, Germany

[21] Appl. No.: 820,061

[22] Filed: Jul. 28, 1977

[30] Foreign Application Priority Data

Aug. 17, 1976 [DE] Fed. Rep. of Germany ....... 2637008

[51] Int. Cl.² .................. A01N 9/36; C07F 9/165
[52] U.S. Cl. ................................. 424/212; 260/941
[58] Field of Search ................... 260/941; 424/212

[56] References Cited

U.S. PATENT DOCUMENTS 3,632,692  1/1972  Morales .................. 260/941 X
3,644,601  2/1972  Miller et al. .............. 260/941 X
3,733,376  5/1973  Kristiansen et al. .......... 260/941 OR

FOREIGN PATENT DOCUMENTS 654,748  8/1941  Belgium.
1,199,251  3/1966  Fed. Rep. of Germany.

OTHER PUBLICATIONS

Abstract of Belgian Pat. 755,934, 3/1971.

Primary Examiner—Anton H. Sutto
Attorney, Agent, or Firm—Burgess, Dinklage & Sprung

[57] ABSTRACT

Novel O-methyl-O-n-propyl-O-(2-carbalkoxy-2-alkoxy-vinyl)-thionophosphoric acid esters of the formula

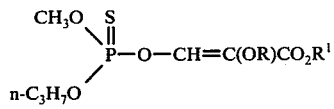

in which
R and $R^1$, which may be identical or different, each represent alkyl, which possess arthropodicidal properties.

9 Claims, No Drawings

COMBATING ARTHROPODS WITH O-METHYL-O-N-PROPYL-O-(2-CARBALKOXY-2-ALKOXY-VINYL)-THIONOPHOSPHORIC ACID ESTERS

The present invention relates to and has for its objects the provision of particular new O-methyl-O-n-propyl-O-(2-carbalkoxy-2-alkoxy-vinyl)-thionophosphoric acid esters which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It has been disclosed in Belgian Patent Specification No. 755,934 and German Published Specification DOS No. 1,199,251 that certain symmetrical O,O-dialkyl-O-vinyl-(thiono)-phosphoric acid esters, for example O,O-diethyl-O-(2-ethoxy-2-carbethoxy-vinyl)-thiono-(Compound A) and O,O-diethyl-O-(1-ethoxy-2-carbethoxy-vinyl)-phosphoric acid esters (Compound B), and in Belgian Patent Specification No. 654,748 that O-ethyl-O-(2-carbethoxy-2-cyano-1-methyl-vinyl)-ethanephosphonic acid ester (Compound C) possess insecticidal and acaricidal properties.

The present invention provides as new compounds, the asymmetrical O,O-dialkyl-O-vinylthionophosphoric acid esters of the general formula

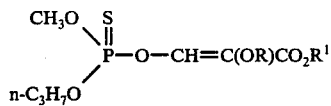

in which
R and R$^1$ each independently is alkyl.

Preferably, R and R$^1$ are alkyl with 1 to 6, especially 1 to 4, carbon atoms.

The general formula (I) includes the corresponding cis- and trans-isomers of the structures (II) and (III) and the mixtures of these isomers:

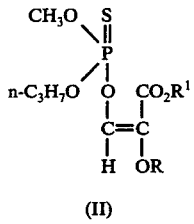 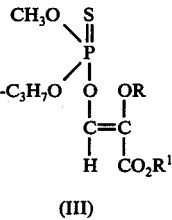

Surprisingly, the asymmetrical O,O-dialkyl-O-vinylthionophosphoric acid esters according to the invention exhibit a better insecticidal and acaricidal action than the known symmetrical O,O-dialkyl-O-vinyl(thiono)-phosphoric acid esters and the O-alkyl-O-vinylphosphonic acid esters of analogous structure and of the same type of action. The compounds according to the present invention thus represent a genuine enrichment of the art.

The invention also provides a process for the preparation of an asymmetrical O,O-dialkyl-O-vinylthionophosphoric acid ester of the formula (I), in which an O-methyl-O-n-propylthionophosphoric acid diester halide of the general formula

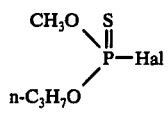

in which
Hal denotes halogen, preferably chlorine, is reacted with a 1-alkoxy-1-formyl-acetic acid ester derivative of the general formula

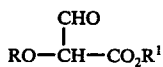

and/or its enol form of the formula

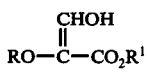

in which
R and R$^1$ have the above-mentioned meanings,
if appropriate in the presence of an acid acceptor and, if appropriate, in the presence of a solvent or diluent.

If, for example, O-methyl-O-n-propyl-thionophosphoric acid diester chloride and 1-ethoxy-1-formyl-acetic acid isopropyl ester are used as starting materials, the course of the reaction can be represented by the following equation:

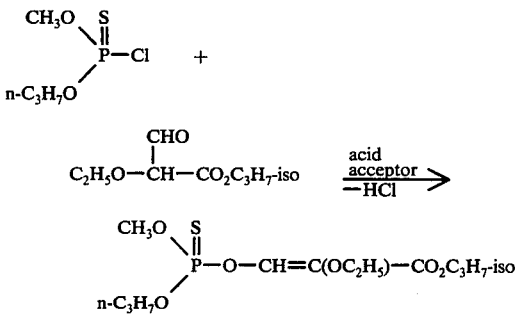

The O-methyl-O-n-propyl-thionophosphoric acid diester halides (IV) required as starting materials are known and can be prepared in accordance with processes known from the literature, as can the 1-alkoxy-1-formylacetic acid ester derivatives (V) and (Va), which are prepared by condensing 1-alkoxyacetic acid alkyl esters with formic acid alkyl esters, if appropriate in the presence of an alcoholate.

The following may be mentioned as individual examples of the 1-alkoxy-1-formyl-acetic acid ester derivatives (V): 1-methoxy-, 1-ethoxy-, 1-n-propoxy-, 1-isopropoxy-, 1-n-butoxy-, 1-sec.-butoxy- and 1-isobutoxy-1-formylacetic acid methyl ester, ethyl ester, n-propyl ester, isopropyl ester, n-butyl ester, isobutyl ester and sec.-butyl ester.

The process for the preparation of the compounds according to the invention is preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate, ethylate or tert.-butylate, have proved particularly suitable, as have aliphatic, aromatic or heterocyclic amines, for example triethylamine, trimethylamine, dimethylaniline, dimethylbenzylamine or pyridine.

The reaction temperature can be varied within a substantial range. In general, the reaction is carried out at from 0° to 100° C., preferably at from 10° to 60° C.

In general, the reaction is allowed to take place under normal pressure.

In a preferred embodiment of the process, the 1-alkoxy-1-formylacetic acid ester derivative, preferably in 6 to 20% excess, is initially introduced, together with the acid acceptor, into one of the above-mentioned solvents, and the O-methyl-O-n-propylthionophosphoric acid diester halide is added dropwise to the mixture. After completion of the reaction an organic solvent, for example toluene, is added, and the organic phase is worked up in the usual manner by washing and drying it, and distilling off the solvent.

The new compounds are obtained in the form of oils which in most cases cannot be distilled without decomposition but are freed from the last volatile constituents by so-called "slight distillation", that is to say by prolonged heating under reduced pressure to moderately elevated temperatures, and are purified in this manner. They are characterized by the refractive index.

As already mentioned, the asymmetrical O,O-dialkyl-O-vinylthionophosphoric acid esters according to the invention are distinguished by an excellent insecticidal and acaricidal activity. They are active against plant pests, pests harmful to health and pests of stored products. They combine a low phytotoxicity with a good action against both sucking and biting insects and mites.

For this reason, the compounds according to the invention can be employed successfully as pesticides in plant protection as well as in the hygiene field and the field of protection of stored products.

The active compounds are well tolerated by plants, have a favorable level of toxicity to warm-blooded animals, and can be used for combating arthropod pests, especially insects and arachnids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.; from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.; from the order of the Anoplura, for example *Phylloxera vastatrix, Pemphigus* spp., *Pediculus humanus corporis, Haematopinus* spp. and *Linognathus* spp.; from the order of the Mallophaga, for example *Trichodectes* spp. and *Damalinea* spp.; from the order of the Thysanoptera, for example *Hercinothrips femoralis* and *Thrips tabaci;* from the order of the Heteroptera, for example *Eurygaster* spp.; *Dysdercus intermedius, Piesma quadrata, Cimex lectularius, Rhodnius prolixus* and *Triatoma* spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella auranti, Aspidiotus hederae, Pseudococcus* spp. and *Psylla* spp.; from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the Hymenoptera, for example *Diprion* spp., *Hoplocampa* spp., *Lasius* spp., *Monomorium pharaonis* and *Vespa* spp.; from the order of the Diptera, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the Siphonaptera, for example *Xenopsylla cheopis* and *Ceratophyllus* spp.; from the class of the Arachnida, for example *Scorpio maurus* and *Latrodectus mactans;* from the order of the Acarina, for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp, *Sarcoptes* spp., *Tarsonemus* spp., *Bryobia praetiosa, Panonychus* spp. and *Tetranychus* spp..

The plant-parasitic nematodes include *Pratylenchus* spp., *Radopholus similis, Ditylenchus dipsaci, Tylenchulus semipenetrans, Heterodera* spp., *Meloidogyne* spp., *Aphelenchoides* spp., *Longidorus* spp., *Xiphinema* spp. and *Trichodorus* spp..

The active compounds can be converted to the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans and fumigating coils, as well as ULV cold mist and warm mist formulations.

These formulations are produced in known manner, for example by mixing the active compounds with extenders, that is to say, liquid or solid or liquefied gaseous diluents or carriers, optionally with the use of surface-active agents, that is to say, emulsifying agents and/or dispersing agents and/or foaming agents. In the case of the use of water as an extender, organic solvents can, for example, also be used as auxiliary solvents.

As liquid diluents or carriers, especially solvents, there are suitable in the main, aromatic hydrocarbons, such as xylene, toluene, benzene or alkyl-naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as dichlorodifluoromethane or trichlorofluoromethane.

As solid carriers there are preferably used ground natural minerals, such as kaolins, clays, talc, chalk, quartz, attapulgite, montmorillonite or diatomaceous earth, and ground synthetic minerals, such as highly dispersed silicic acid, alumina and silicates.

Preferred examples of emulsifying and foam-forming agents include nonionic and anionic emulsifiers, such as polyoxyethylene-fatty acid esters, polyoxyethylene-fatty alcohol ethers, for example alkylaryl polyglycol ethers, alkyl sulphonates, alkyl sulphates and aryl sulphonates as well as albumin hydrolysis products; and preferred examples of dispersing agents include lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain from 0.1 to 95 percent by weight of active compound, preferably between 0.5 and 90 percent.

The active compounds according to the invention may be used in the form of their formulations of the types that are commercially available formulations or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds are employed in a customary manner appropriate for the use forms.

When used against pests harmful to health and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperature and pressures, such as halogenated hydrocarbons, e.g. dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylene, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethylsulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl or polyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, bactericides, fungicides, rodenticides, herbicides, fertilizers, growth-regulating agents, bird repellents, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaridically effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1 a. The 1-alkoxy-1-formyl-acetic acid alkyl esters required as starting compounds were prepared, for example, as follows:

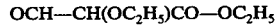

OCH—CH(OC$_2$H$_5$)CO—OC$_2$H$_5$ 112 g (1 mol) of potassium tert.-butylate were added incrementally to a mixture of 132 g (1 mol) of ethoxyacetic acid ethyl ester and 81.5 g (1.1 mol) of formic acid ethyl ester, in such a way that the reaction temperature did not exceed 40° C. The reaction mixture was then stirred further for 4 hours at 20° C., after which it was poured into 1 liter of water and extracted once with 200 ml of methylene chloride. The methylene chloride extract was discarded and the aqueous phase was acidified with hydrochloric acid while cooling with ice, and was extracted with methylene chloride. After drying the extract over sodium sulphate, the methylene chloride was stripped off. 103 g (64% of theory) of 1-ethoxy-1-formyl-acetic acid ethyl ester having a refractive index $n_D^{24}$ of 1.4452 were obtained.

The following compounds could be synthesized analogously:

| | |
|---|---|
| OCH—CH(OC$_2$H$_5$)CO—OCH$_3$ | in 51% yield with a refractive index of $n_D^{21}$: 1.4398 |
| OCH—CH(OC$_3$H$_7$-iso)CO—OC$_2$H$_5$ | in 65% yield with a refractive index of $n_D^{21}$: 1.4484 |
| OCH—CH(OC$_3$H$_7$-iso)CO—OC$_3$H$_7$-iso | in 67% yield with a refractive index of $n_D^{20}$: 1.4400 |
| OCH—CH(OC$_3$H$_7$-iso)CO—OCH$_3$ | in 35% yield with a refractive index of $n_D^{20}$: 1.4470 |
| OCH—CH(OCH$_3$)CO—OC$_2$H$_5$ | in 51% yield with a refractive index of $n_D^{19}$: 1.4370 |
| OCH—CH(OCH$_3$)CO—OCH$_3$ | in 39% yield with a refractive index of $n_D^{24}$: 1.4422 | b) 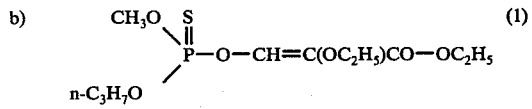 (1)

18.8 g (0.1 mol) of O-methyl-O-n-propylthionophosphoric acid ester chloride were added dropwise to a mixture of 17.6 g (0.11 mol) of 1-ethoxy-1-formyl-acetic acid ethyl ester and 16 g (0.115 mol) of potassium carbonate in 200 ml of acetonitrile. The mixture was allowed to continue to react for 3 hours at 40° C., after which the reaction mixture was poured into 300 ml of toluene. The toluene solution was washed with saturated sodium bicarbonate solution and with water and was dried over sodium sulphate. The solvent was then stripped off and the residue was subjected to slight distillation. 23 g (74% of theory) of O-methyl-O-n-propyl-O-(2-carbethoxy-2-ethoxy-vinyl)-thionophosphoric acid ester were obtained in the form of a yellow oil having a refractive index $n_D^{25}$ of 1.4690.

The following compounds of the formula $$\begin{array}{c} CH_3O \\ \diagdown \\ n\text{-}C_3H_7O \end{array} \!\!\! \begin{array}{c} S \\ \| \\ P\text{---}O\text{---}CH=C(OR)CO\text{---}OR^1 \end{array} \quad (I)$$

were synthesized analogously:

Table 1

| Compound No. | R | R¹ | Yield (% of theory) | Refractive index: |
|---|---|---|---|---|
| 2 | $C_2H_5$ | $CH_3$ | 33 | $n_D^{23}$: 1.4760 |
| 3 | iso-$C_3H_7$ | iso-$C_3H_7$ | 99 | $n_D^{23}$: 1.4679 |
| 4 | iso-$C_3H_7$ | $CH_3$ | 80 | $n_D^{23}$: 1.4700 |
| 5 | iso-$C_3H_7$ | $C_2H_5$ | 82 | $n_D^{20}$: 1.4689 |
| 6 | $CH_3$ | $CH_3$ | 56 | $n_D^{22}$: 1.4780 |
| 7 | $CH_3$ | $C_2H_5$ | 77 | $n_D^{25}$: 1.4727 |

In the following examples the active compounds according to the present invention are identified by the number given in brackets and the known comparison compounds are identified as follows:

$$\text{(B)} = (C_2H_5O)_2\overset{\overset{O}{\|}}{P}\text{---}O\text{---}\overset{\overset{OC_2H_5}{|}}{C}=CH\text{---}COOC_2H_5$$

$$\text{(C)} = \begin{array}{c} C_2H_5O \\ \diagdown \\ C_2H_5 \end{array}\!\!\overset{\overset{O}{\|}}{P}\text{---}O\text{---}\overset{\overset{CH_3}{|}}{C}=\overset{\overset{}{|}}{\underset{CN}{C}}\text{---}COOC_2H_5$$

$$\text{(A)} = (C_2H_5O)_2\overset{\overset{S}{\|}}{P}\text{---}O\text{---}CH=\overset{\overset{OC_2H_5}{|}}{C}\text{---}COOC_2H_5$$

EXAMPLE 2

Test insects: *Blatta orientalis*
Solvent: Acetone

The active compound was taken up in the solvent in an amount of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 10 test insects were then placed in the Petri dish and it was covered with a glass lid.

The condition of the test insects was observed 3 days after the commencement of the experiments. The destruction, in %, was determined. 100% denoted that all the test insects had been killed; 0% denoted that no test insects had been killed.

The active compounds, the concentrations of the active compounds, the test insects and the results can be seen from the following table:

Table A

| | (*Blatta orientalis*) | |
|---|---|---|
| Active compound | Active compound concentration of the solution in % | Degree of destruction in % |
| (B) | 0.2 | 0 |
| (C) | 0.2 | 0 |
| (6) | 0.2 | 100 |
| (7) | 0.2 | 100 |
| (2) | 0.2 | 100 |
| (4) | 0.2 | 100 |
| (1) | 0.2 | 100 |
| (5) | 0.2 | 100 |
| (3) | 0.2 | 100 |

EXAMPLE 3

Test insects: *Sitophilus granarius*
Solvent: Acetone

The active compound was taken up in the solvent in an amount of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denoted that all the test insects had been killed; 0% denoted that no test insects had been killed.

The active compounds, the concentrations of the active compounds, the test insects and the results can be seen from the following table:

Table 3

| | (*Sitophilus granarius*) | |
|---|---|---|
| Active compound | Active compound concentration of the solution in % | Degree of destruction in % |
| (B) | 0.2 | 100 |
| | 0.02 | 80 |
| (C) | 0.2 | 0 |
| (2) | 0.02 | 100 |
| | 0.002 | 100 |
| (4) | 0.02 | 100 |
| | 0.002 | 60 |
| (1) | 0.02 | 100 |
| | 0.002 | 100 |
| (5) | 0.02 | 100 |
| | 0.002 | 50 |
| (3) | 0.02 | 100 |
| | 0.002 | 50 |

EXAMPLE 4

Plutella test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamondback moth (*Plutella maculipennis*).

After the specified periods of time, the degree of destruction was determined as a percentage: 100% meant that all the caterpillars were killed whereas 0% meant that none of the caterpillars were killed.

The active compounds, the concentrations of the active compounds, the evaluation times and the results can be seen from the following table:

Table 4

| Active compound | (*Plutella* test) | |
|---|---|---|
| | Active compound concentration in % | Degree of destruction in % after 3 days |
| (B) | 0.1 | 100 |
| | 0.01 | 0 |
| (6) | 0.1 | 100 |
| | 0.01 | 100 |
| (2) | 0.1 | 100 |
| | 0.01 | 100 |
| (4) | 0.1 | 100 |
| | 0.01 | 100 |
| (7) | 0.1 | 100 |
| | 0.01 | 100 |
| (1) | 0.1 | 100 |
| | 0.01 | 100 |
| (5) | 0.1 | 100 |
| | 0.01 | 100 |
| (3) | 0.1 | 100 |
| | 0.01 | 100 |

EXAMPLE 5

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all the spider mites were killed whereas 0% meant that none of the spider mites were killed.

The active compounds, the concentrations of the active compounds, the evaluation times and the results can be seen from the following table:

Table 5

| Active compound | (*Tetranychus* test) | |
|---|---|---|
| | Active compound concentration in % | Degree of destruction in % after 2 days |
| (A) | 0.1 | 98 |
| | 0.01 | 0 |
| (6) | 0.1 | 99 |
| | 0.01 | 80 |
| (2) | 0.1 | 99 |
| | 0.01 | 60 |
| (7) | 0.1 | 99 |

Table 5-continued

| Active compound | (*Tetranychus* test) | |
|---|---|---|
| | Active compound concentration in % | Degree of destruction in % after 2 days |
| | 0.01 | 50 |

It will be appreciated that the instant specification and examples are set forth by way of illustration and not limitation, and that various modifications and changes may be made without departing from the spirit and scope of the present invention.

What is claimed is:

1. An O-methyl-O-n-propyl-O-(2-carbalkoxy-2-alkoxy-vinyl)-thionophosphoric acid ester of the formula

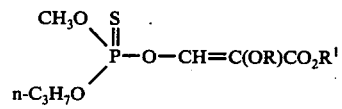

in which
R and R¹ each independently is alkyl with 1 to 6 carbon atoms.

2. A method of combating arthropods which comprises applying to the arthropods, or to a habitat thereof, an arthropodicidally effective amount of a compound according to claim 1.

3. An arthropodicidal composition containing as active ingredient an arthropodicidally effective amount of a compound according to claim 1 in admixture with a diluent.

4. A compound according to claim 1 wherein said compound is
O-methyl-O-n-propyl-O-(2-carbethoxy-2-ethoxy-vinyl)-thionophosphoric acid ester of the formula

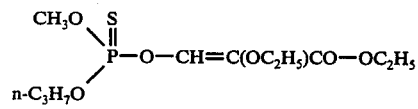

5. A compound according to claim 1 wherein said compound is
O-methyl-O-n-propyl-O-(2-carbomethoxy-2-ethoxy-vinyl)-thionophosphoric acid ester of the formula

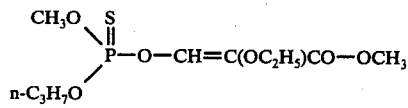

6. A compound according to claim 1 wherein said compound is
O-methyl-O-n-propyl-O-(2-carbisopropoxy-2-isopropoxy-vinyl)-thionophosphoric acid ester of the formula

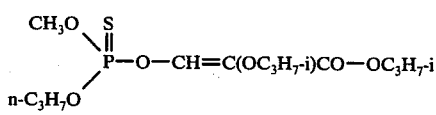

7. A compound according to claim 1 wherein said compound is

O-methyl-O-n-propyl-O-(2-carbomethoxy-2-iso-
propoxy-vinyl)-thionophosphoric acid ester of the
formula

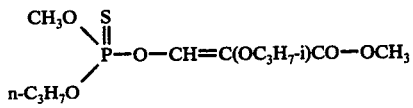

8. A compound according to claim 1 wherein said compound is

O-methyl-O-n-propyl-O-(2-carbethoxy-2-methoxy-vinyl)-thionophosphoric acid ester of the formula

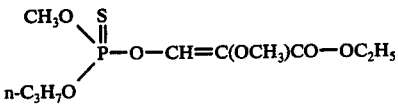

9. The method according to claim 2 in which said compound is
O-methyl-O-n-propyl-O-(2-carbethoxy-2-ethoxy-vinyl)-thionophosphoric acid ester,
O-methyl-O-n-propyl-O-(2-carbomethoxy-2-ethoxy-vinyl)-thionophosphoric acid ester,
O-methyl-O-n-propyl-O-(2-carbisopropoxy-2-iso-propoxy-vinyl)-thionophosphoric acid ester,
O-methyl-O-n-propyl-O-(2-carbomethoxy-2-iso-propoxy-vinyl)-thionophosphoric acid ester or
O-methyl-O-n-propyl-O-(2-carbethoxy-2-methoxy-vinyl)-thionophosphoric acid ester.

* * * * *